(12) United States Patent
Köcher et al.

(10) Patent No.: US 8,791,200 B2
(45) Date of Patent: *Jul. 29, 2014

(54) TCD BASED HYDROPHILIC POLYURETHANE DISPERSIONS

(75) Inventors: Jürgen Köcher, Langenfeld (DE); Christian Wamprecht, Neuss (DE)

(73) Assignee: Bayer MaterialScience AG, Monheim (DE)

( * ) Notice: Subject to any disclaimer, the term of this patent is extended or adjusted under 35 U.S.C. 154(b) by 200 days.

This patent is subject to a terminal disclaimer.

(21) Appl. No.: 13/062,267

(22) PCT Filed: Aug. 22, 2009

(86) PCT No.: PCT/EP2009/006102
§ 371 (c)(1),
(2), (4) Date: Mar. 17, 2011

(87) PCT Pub. No.: WO2010/025841
PCT Pub. Date: Mar. 11, 2010

(65) Prior Publication Data
US 2012/0083537 A1  Apr. 5, 2012

(30) Foreign Application Priority Data
Sep. 4, 2008 (EP) .................................. 08015574

(51) Int. Cl.
C08G 18/08 (2006.01)

(52) U.S. Cl.
USPC ........... 524/591; 524/589; 524/590; 524/839; 524/840; 528/49; 528/59; 528/61; 528/64; 528/85

(58) Field of Classification Search
USPC ........... 524/589, 590, 591, 839, 840; 528/49, 528/64, 61, 59, 85
See application file for complete search history.

(56) References Cited

U.S. PATENT DOCUMENTS

| | | | |
|---|---|---|---|
| 3,857,809 A | 12/1974 | Oertel et al. | |
| 3,900,688 A | 8/1975 | Thoma et al. | |
| 4,675,211 A | 6/1987 | Thoma et al. | |
| 5,041,100 A | 8/1991 | Rowland et al. | |
| 5,061,424 A | 10/1991 | Karimi et al. | |
| 5,177,141 A | 1/1993 | Thoma et al. | |
| 5,589,563 A * | 12/1996 | Ward et al. ................... | 528/44 |
| 5,962,620 A | 10/1999 | Reich et al. | |
| 6,586,523 B1 | 7/2003 | Blum et al. | |
| 6,642,303 B2 * | 11/2003 | Schutze et al. .............. | 524/589 |
| 6,656,517 B2 | 12/2003 | Michal et al. | |
| 7,276,554 B2 | 10/2007 | Rische et al. | |
| 7,452,525 B1 * | 11/2008 | Berezkin et al. ............. | 424/59 |
| 7,642,334 B2 * | 1/2010 | Uchida et al. ................ | 528/195 |
| 8,318,761 B2 | 11/2012 | Svenstrup et al. | |
| 2003/0203991 A1 | 10/2003 | Schottman et al. | |
| 2005/0054774 A1 | 3/2005 | Kangas | |
| 2006/0040253 A1 | 2/2006 | Roberts et al. | |
| 2006/0128885 A1 | 6/2006 | Rische et al. | |
| 2006/0212106 A1 | 9/2006 | Weber et al. | |
| 2007/0167565 A1 | 7/2007 | Rische et al. | |
| 2007/0254974 A1 | 11/2007 | Mager et al. | |
| 2008/0044474 A1 | 2/2008 | Dorr et al. | |
| 2008/0188625 A1 * | 8/2008 | Uchida et al. ............... | 525/403 |
| 2009/0252699 A1 | 10/2009 | Kocher et al. | |
| 2009/0252804 A1 | 10/2009 | Koecher et al. | |
| 2011/0015724 A1 | 1/2011 | Kocher et al. | |
| 2011/0021696 A1 | 1/2011 | Kocher et al. | |
| 2011/0022005 A1 | 1/2011 | Kocher | |
| 2011/0160310 A1 | 6/2011 | Kocher et al. | |
| 2012/0083537 A1 | 4/2012 | Kocher et al. | |

FOREIGN PATENT DOCUMENTS

| | | |
|---|---|---|
| DE | 2221798 A1 | 11/1973 |
| DE | 2252280 A1 | 5/1974 |
| DE | 19914885 A1 | 10/2000 |
| EP | 0125466 A2 | 11/1984 |
| JP | 2002-128859 A | 5/2002 |
| WO | WO-99/38545 A1 | 8/1999 |
| WO | WO-2006/037321 A1 | 4/2006 |
| WO | WO-2006/093355 A1 | 9/2006 |
| WO | WO-2006/101573 A1 | 9/2006 |
| WO | WO-2006/109816 A1 | 10/2006 |
| WO | WO-2007/101573 A1 | 9/2007 |

OTHER PUBLICATIONS

Ullmann's Enzyklopädie der technischen Chemie, 4th edition, vol. 19, Verlag Chemie, Weinheim, pp. 31-38, 1980.

* cited by examiner

*Primary Examiner* — Michael L Leonard
(74) *Attorney, Agent, or Firm* — Drinker Biddle & Reath LLP

(57) ABSTRACT

The present invention relates to a polyurethaneurea solution having a polyurethaneurea having a structural unit of the formula (I)

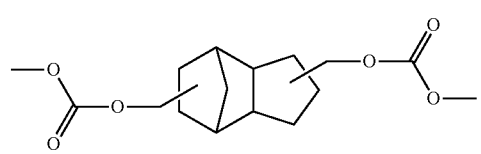

and terminated with at least one copolymer unit of the group consisting of a polyethylene oxide, a polypropylene oxide, and mixtures thereof.

12 Claims, No Drawings

TCD BASED HYDROPHILIC POLYURETHANE DISPERSIONS

CROSS-REFERENCE TO RELATED APPLICATIONS

This application is a national stage application (under 35 U.S.C. §371) of PCT/EP2009/006102, filed Aug. 22, 2009, which claims benefit of European application 08015574.0 filed Sep. 4, 2008.

BACKGROUND OF THE INVENTION

The present invention relates to innovative polyurethaneurea solutions which can be used for producing hydrophilic coatings on a very wide variety of substrates.

Particularly in the medical sector, hydrophilic coatings on surfaces of medical devices are important since their use can be greatly improved as a result. The insertion and displacement of urinary or blood-vessel catheters is made easier by the fact that hydrophilic surfaces in contact with blood or urine adsorb a film of water. This reduces the friction between the catheter surface and the vessel walls, and so the catheter is easier to insert and move. Direct watering of the devices prior to the intervention can also be performed in order to reduce friction through the formation of a homogeneous water film. The patients concerned experience less pain and the risk of injuries to the vessel walls is reduced by such measures. Furthermore, when catheters are being used, there is always the risk of formation of blood clots. In this context, hydrophilic coatings are generally considered to be useful for anti-thrombogenic coatings.

Suitable in principle for producing such surfaces are polyurethane coatings which are produced starting from solutions or dispersions of corresponding polyurethanes.

For instance, U.S. Pat. No. 5,589,563 describes the use of coatings having surface-modified end groups for polymers that are used in the biomedical sector, and these coatings can also be used to coat medical devices. The resulting coatings are produced starting from solutions or dispersions, and the polymeric coatings comprise different end groups, selected from amines, fluorinated alkanols, polydimethylsiloxanes and amine-terminated polyethylene oxides. As a coating for medical devices, however, these polymers do not have satisfactory properties, particularly as regards the required hydrophilicity.

A disadvantage of aqueous dispersions of the kind described in publications including U.S. Pat. No. 5,589,563, moreover, is that the size of the dispersed particles makes the coatings relatively rough. Furthermore, the resulting coatings from aqueous dispersions generally lack sufficient stability. Consequently, there is a need for hydrophilic coating systems which exhibit outstanding hydrophilicity in conjunction with a relatively smooth surface and a high stability.

Polyurethane solutions per se are known from the prior art, but—with the exception of the aforementioned polyurethane solutions of U.S. Pat. No. 5,589,563—have not been used for coating medical devices.

Thus, for example, DE 22 21 798 A describes a process for preparing stable and lightfast solutions of polyurethaneureas from prepolymers with terminal isocyanate groups and diamines in solvents of low polarity, by reacting prepolymers of a) substantially linear polyhydroxyl compounds having molecular weights of about 500 to 5000,
b) if desired, dihydroxy compounds of low molecular weight, and
c) aliphatic and/or cycloaliphatic diisocyanates, the molar ratio of hydroxyl to isocyanate groups being between about 1:1.5 and 1:5, in a solvent (mixture) of optionally chlorinated aromatic and/or chlorinated aliphatic hydrocarbons and primary, secondary and/or tertiary aliphatic and/or cycloaliphatic alcohols with diamines as chain extenders, at least 80 mol % of the chain extender being 1,4-diamino-cyclohexane with a cis/trans isomer ratio of between 10/90 and 60/40. These polyurethaneurea solutions are used for producing lightfast films and coatings.

Furthermore, DE 22 52 280 A describes a process for coating textile substrates by the reverse method with adhesion coats and top coats comprising solutions of aliphatic, segmented polyurethane elastomers, which are polycarbonate-containing.

Furthermore, EP 0 125 466 A describes a process for the multiple reverse coating of textile substrates, preferably in web form, for producing synthetic leather, from at least one top coat solution and at least one adhesion coat solution on the basis of polyurethanes.

European Application No. 08153055.2, unpublished at the priority date of the present specification, discloses hydrophilic coatings of polyurethaneureas which are based on a specific combination of polycarbonate polyols as synthesis components and copolymers of ethylene oxide and propylene oxide as end groups.

It has now been found that the mechanical properties of these coatings can be improved by using in the polycarbonate polyol component according to European Application No. 08153055.2, unpublished at the priority date of the present specification, polycarbonate polyols which have structural units of the formula (I)

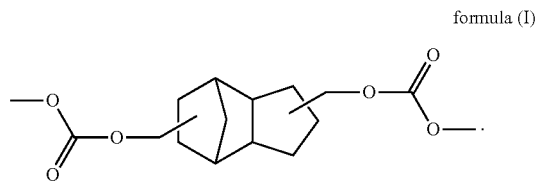

formula (I)

BRIEF DESCRIPTION OF THE INVENTION

The present invention accordingly provides polyurethaneurea solutions comprising at least one polyurethaneurea which has structural units of the formula (I)

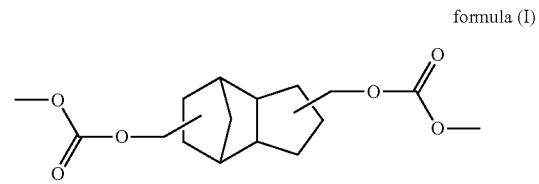

formula (I)

and is terminated with at least one copolymer unit of polyethylene oxide and polypropylene oxide.

The surface coatings obtainable by the solutions according to the invention are notable for high hydrophilicity, a smooth surface and a high stability, and so are able to reduce, for example, the formation of blood clots during treatment with the medical device.

Polyurethaneureas for the purposes of the present invention are polymeric compounds which have (a) at least two repeating units containing urethane groups, of the following general structure

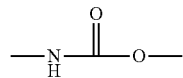

and (b) at least one repeating unit containing urea groups:

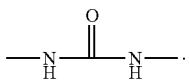

The solutions according to the invention are based on polyurethaneureas of the aforementioned kind which have substantially no ionic or ionogenic modification. By this is meant, in the context of the present invention, that the polyurethaneureas for use in accordance with the invention have substantially no ionic groups, such as, in particular, no sulphonate, carboxylate, phosphate and phosphonate groups.

The term "substantially no ionic groups" means, in the context of the present invention, that the resulting coating of the polyurethaneurea has ionic groups with a fraction of in general not more than 2.50% by weight, in particular not more than 2.00% by weight, preferably not more than 1.50% by weight, more preferably not more than 1.00% by weight, especially not more than 0.50% by weight, more especially no ionic groups. Hence it is preferred in particular that the polyurethaneurea has no ionic groups, since high concentrations of ions in organic solution mean that the polymer is no longer sufficiently soluble and hence that no stable solutions can be obtained. If the polyurethane used in accordance with the invention does have ionic groups, the groups in question are preferably carboxylates and sulphonates.

DETAILED DESCRIPTION OF THE INVENTION

The polyurethaneureas of the aforementioned kind that are essential to the invention are preferably substantially linear molecules, but may also be branched, although this is less preferred. Substantially linear molecules in the context of the present invention are systems with low levels of incipient crosslinking, the parent polycarbonate polyol component having an average hydroxy functionality of preferably 1.7 to 2.3, more preferably 1.8 to 2.2, very preferably 1.9 to 2.1.

The number-average molecular weight of the polyurethaneureas that are essential to the invention is preferably 1000 to 200 000 g/mol, more preferably from 5000 to 100 000 g/mol. This number-average molecular weight is measured against polystyrene as standard in dimethylacetamide at 30° C.

The solutions according to the invention are prepared by reacting synthesis components which comprise at least one polycarbonate polyol component a), at least one polyisocyanate component b), at least one polyoxyalkylene ether component c), at least one diamine and/or amino alcohol component d) and optionally a further polyol component.

The invention therefore likewise provides a process for preparing the solutions according to the invention, in which a polycarbonate polyol component a), at least one polyisocyanate component b), at least one polyoxyalkylene ether component c), at least one diamine and/or amino alcohol component d) and, if desired, a further polyol component are reacted with one another.

Component a) comprises at least one polycarbonate polyol a1), which is obtained by reacting carbonic acid derivatives such as diphenyl carbonate, dimethyl carbonate or phosgene with difunctional alcohols of the formula (II)

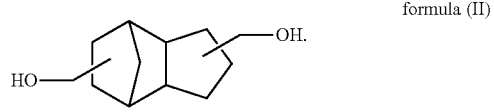

formula (II)

For the preparation in a pressure reactor and at elevated temperature, TCD Alcohol DM [3(4),8(9)-bis(hydroxymethyl)tricyclo(5.2.1.0/2.6)decane/tricyclodecanedimethanol] is reacted with diphenyl carbonate, dimethyl carbonate or phosgene. Reaction with dimethyl carbonate is preferred. Where dimethyl carbonate is used, the methanol elimination product is removed by distillation in a mixture with excess dimethyl carbonate.

These polycarbonate polyols a1) based on diols of the formula (II) have molecular weights, determined through the OH number, of preferably 200 to 10 000 g/mol, more preferably 300 to 8000 g/mol and very preferably 400 to 6000 g/mol.

Component a) is preferably a mixture of the aforementioned polycarbonate polyols a1) based on diols of the formula (II) and further polycarbonate polyols a2).

Such further polycarbonate polyols a2) preferably have average hydroxyl functionalities of 1.7 to 2.3, more preferably of 1.8 to 2.2, very preferably of 1.9 to 2.1.

Furthermore, the polycarbonate polyols a2) have molecular weights, determined through the OH number, of preferably 400 to 6000 g/mol, more preferably 500 to 5000 g/mol, in particular of 600 to 3000 g/mol, which are obtainable, for example, by reaction of carbonic acid derivatives, such as diphenyl carbonate, dimethyl carbonate or phosgene, with polyols, preferably diols. Suitable such diols include, for example, ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentane-1,3-diol, di-, tri- or tetraethylene glycol, dipropylene glycol, polypropylene glycols, dibutylene glycol, polybutylene glycols, bisphenol A, tetrabromobisphenol A, and also lactone-modified diols.

These polycarbonate polyols a2) contain preferably 40% to 100% by weight of hexanediol, preferably 1,6-hexanediol and/or hexanediol derivatives, preferably those which as well as terminal OH groups have ether groups or ester groups, examples being products obtained by reacting 1 mol of hexanediol with at least 1 mol, preferably 1 to 2 mol of caprolactone or by etherifying hexanediol with itself to give the dihexylene or trihexylene glycol, as synthesis components. Polyether-polycarbonate diols can be used as well. The hydroxyl polycarbonates ought to be substantially linear. Where appropriate, however, they may be slightly branched as a result of the incorporation of polyfunctional components, especially low molecular weight polyols. Examples of polyols suitable for this purpose include glycerol, hexane-1,2,6-triol, butane-1,2,4-triol, trimethylolpropane, pentaerythritol, quinitol, mannitol, sorbitol, methylglycoside or 1,3,4,6-dianhydrohexitols. Preference is given to such polycarbonates a2) based on hexane-1,6-diol and also on modifying co-diols such as for example, butane-1,4-diol or else on ε-caprolactone. Further preferred polycarbonate diols a2) are those based on mixtures of hexane-1,6-diol and butane-1,4-diol.

In one preferred embodiment, a mixture is used in a) of the polycarbonate polyols a1) and those polycarbonate polyols a2) based on hexane-1,6-diol, butane-1,4-diol or mixtures thereof.

In the case of mixtures of the constituents a1) and a2), the fraction of a1) as a proportion of the mixture is preferably at least 5 mol %, more preferably at least 10 mol %, based on the total molar amount of polycarbonate.

The polyurethaneureas essential to the invention additionally have units which derive from at least one polyisocyanate as synthesis component b).

As polyisocyanate b) it is possible to use all of the aromatic, araliphatic, aliphatic and cycloaliphatic isocyanates that are known to the person skilled in the art and have an average NCO functionality ≥1, preferably ≥2, individually or in any desired mixtures with one another, it being immaterial whether they have been prepared by phosgene processes or phosgene-free processes. They may also have iminooxadiazinedione, isocyanurate, uretdione, urethane, allophanate, biuret, urea, oxadiazinetrione, oxazolidinone, acylurea and/or carbodiimide structures. The polyisocyanates may be used individually or in any desired mixtures with one another.

Preference is given to using isocyanates from the series of the aliphatic or cycloaliphatic representatives, having a carbon skeleton (without the NCO groups present) of 3 to 30, preferably 4 to 20 carbon atoms.

Particularly preferred compounds of component b) correspond to the type mentioned above with aliphatically and/or cycloaliphatically attached NCO groups, such as, for example, bis(isocyanatoalkyl)ethers, bis- and tris(isocyanatoalkyl)benzenes, -toluenes, and -xylenes, propane diisocyanates, butane diisocyanates, pentane diisocyanates, hexane diisocyanates (e.g., hexamethylene diisocyanate, HDI, heptane diisocyanates, octane diisocyanates, nonane diisocyanates (e.g. trimethyl-HDI (TMDI) generally in the form of a mixture of the 2,4,4- and 2,2,4-isomers), nonane triisocyanates (e.g. 4-isocyanatomethyl-1,8-octane diisocyanate), decane diisocyanates, decane triisocyanates, undecane diisocyanates, undecane triisocyanates, dodecane diisocyanates, dodecane triisocyanates, 1,3- and 1,4-bis(isocyanatomethyl) cyclohexanes ($H_6$XDI), 3-isocyanatomethyl-3,5,5-trimethylcyclohexyl isocyanate (isophorone diisocyanate, IPDI), bis (4-isocyanatocyclohexyl)methane ($H_{12}$MDI) or bis (isocyanatomethyl)norbornane (NBDI).

Very particularly preferred compounds of component b) are hexamethylene diisocyanate (HDI), Trimethyl-HDI (TMDI), 2-methylpentane-1,5-diisocyanate (MPDI), isophorone diisocyanate (IPDI), 1,3- and 1,4-bis(isocyanatomethyl)cyclohexane ($H_6$XDI), bis(isocyanatomethyl)norbornane (NBDI), 3(4)-isocyanatomethyl-1-methylcyclohexyl isocyanate (IMCI) and/or 4,4'-bis(isocyanatocyclohexyl) methane ($H_{12}$MDI) or mixtures of these isocyanates. Further examples are derivatives of the aforementioned diisocyanates with uretdione, isocyanurate, urethane, allophanate, biuret, iminooxadiazinedione and/or oxadiazinetrione structure and with more than two NCO groups.

The amount of the constituent b) in the preparation of the polyurethaneureas essential to the invention is preferably 1.0 to 3.5 mol, more preferably 1.0 to 3.3 mol, in particular 1.0 to 3.0 mol, based in each case on the amount of the compounds of component a).

The polyurethaneureas essential to the invention have units which derive from a copolymer of polyethylene oxide and polypropylene oxide as synthesis component c). These copolymer units are present in the form of end groups in the polyurethaneurea and have the effect of a particularly advantageous hydrophilicization.

Nonionically hydrophilicizing compounds c) of this kind are, for example, monofunctional polyalkylene oxide polyether alcohols that have on average 5 to 70, preferably 7 to 55, ethylene oxide units per molecule, of the kind obtainable in a manner known per se by alkoxylating suitable starter molecules (e.g. in Ullmanns Enzyklopadie der technischen Chemie, 4th edition, Volume 19, Verlag Chemie, Weinheim, pp. 31-38).

Suitable starter molecules are, for example, saturated monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, such as diethylene glycol monobutyl ether for example, unsaturated alcohols such as allyl alcohol, 1,1-dimethylallyl alcohol or oleyl alcohol, aromatic alcohols such as phenol, the isomeric cresols or methoxyphenols, araliphatic alcohols such as benzyl alcohol, anisyl alcohol or cinnamyl alcohol, secondary monoamines such as dimethylamine, diethylamine, dipropylamine, diisopropylamine, dibutylamine, bis(2-ethylhexyl)amine, N-methyl- and N-ethylcyclohexylamine or dicyclohexylamine and also heterocyclic secondary amines such as morpholine, pyrrolidine, piperidine or 1H-pyrazole. Preferred starter molecules are saturated monoalcohols. Particular preference is given to using diethylene glycol monobutyl ether as starter molecule.

The alkylene oxides, ethylene oxide and propylene oxide, can be used in any order or else in a mixture in the alkoxylation reaction.

The polyalkylene oxide polyether alcohols are mixed polyalkylene oxide polyethers of ethylene oxide and propylene oxide, and preferably at least 30 mol %, more preferably at least 40 mol % of their alkylene oxide units are composed of ethylene oxide units. Preferred nonionic compounds are monofunctional mixed polyalkylene oxide polyethers, which have at least 40 mol % of ethylene oxide units and not more than 60 mol % of propylene oxide units based on the total fraction of alkylene oxide units.

The number-average molar weight of the polyoxyalkylene ether is preferably 500 g/mol to 5000 g/mol, more preferably 1000 g/mol to 4000 g/mol, in particular 1000 to 3000 g/mol.

The amount of constituent c) in the preparation of the polyurethaneureas that are essential to the invention is preferably 0.01 to 0.5 mol, more preferably 0.02 to 0.4 mol, in particular 0.04 to 0.3 mol, based in each case on the amount of the compounds of component a).

In accordance with the invention, it has been possible to show that the polyurethaneureas with end groups which are based on mixed polyoxyalkylene ethers of polyethylene oxide and polypropylene oxide are particularly suitable for producing coatings having a high hydrophilicity.

The polyurethaneureas that are essential to the invention have units which derive from at least one diamine or amino alcohol as a synthesis component, and serve as what are known as chain extenders d).

Such chain extenders are, for example diamines or polyamines and also hydrazides, examples being hydrazine, ethylenediamine, 1,2- and 1,3-diaminopropane, 1,4-diaminobutane, 1,6-diaminohexane, isophoronediamine, isomer mixture of 2,2,4- and 2,4,4-trimethylhexamethylenediamine, 2-methylpentamethylenediamine, diethylenetriamine, 1,3- and 1,4-xylylenediamine, α,α,α',α'-tetramethyl-1,3- and -1,4-xylylenediamine and 4,4'-diaminodicyclohexylmethane, dimethylethylenediamine, hydrazine, adipic dihydrazide, 1,4-bis(aminomethyl)cyclohexane, 4,4'-diamino-3,3'-dimethyldicyclohexylmethane and other ($C_1$-$C_4$)-di- and tetraalkyldicyclohexylmethanes, e.g. 4,4'-diamino-3,5-diethyl-3',5'-diisopropyldicyclohexylmethane.

Suitable diamines or amino alcohols are generally diamines or amino alcohols of low molecular weight which contain active hydrogen whose reactivity towards NCO groups differs, such as compounds which as well as primary amino groups also have secondary amino groups, or as well as an amino group (primary or secondary) also have OH groups. Examples of such compounds are primary and secondary amines, such as 3-amino-1-methylaminopropane, 3-amino-1-ethylaminopropane, 3-amino-1-cyclohexylaminopropane, 3-amino-1-methylaminobutane, and also amino alcohols, such as N-aminoethylethanolamine, ethanolamine, 3-aminopropanol, neopentanolamine and with particular preference diethanolamine.

Constituent d) of the polyurethaneureas that are essential to the invention can be used as a chain extender in their preparation.

The amount of constituent d) in preparing the polyurethaneureas that are essential to the invention is preferably 0.1 to 1.5 mol, more preferably 0.2 to 1.3 mol, in particular 0.3 to 1.2 mol, based in each case on the amount of the compounds of component a).

In a further embodiment, the polyurethaneureas that are essential to the invention comprise additional units which derive from at least one further polyol as a synthesis component.

The further, low molecular weight polyols e) that are used to synthesize the polyurethaneureas generally have the effect of stiffening and/or of branching of the polymer chain. The molecular weight is preferably 62 to 500 g/mol, more preferably 62 to 400 g/mol, in particular 62 to 200 g/mol.

Suitable polyols may contain aliphatic, alicyclic or aromatic groups. Mention may be made here, for example, of the low molecular weight polyols having up to about 20 carbon atoms per molecule, such as, for example, ethylene glycol, diethylene glycol, triethylene glycol, 1,2-propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenyl)propane), hydrogenated bisphenol A (2,2-bis(4-hydroxycyclohexyl)propane), and also trimethylolpropane, glycerol or pentaerythritol and mixtures thereof and also, where appropriate of further low molecular weight polyols. Ester diols can be used as well, such as, for example, α-hydroxybutyl-ε-hydroxycaproic esters, ω-hydroxyhexyl-γ-hydroxybutyric esters, adipic acid (β-hydroxyethyl) esters or terephthalic acid bis(β-hydroxyethyl) ester.

The amount of constituent e) in preparing the polyurethaneureas that are essential to the invention is preferably 0.05 to 1.0 mol, more preferably 0.05 to 0.5 mol, in particular 0.1 to 0.5 mol, based in each case on the amount of the compounds of component a).

The reaction of the isocyanate-containing component b) with the hydroxy- or amine-functional compounds a), c), d) and where appropriate, e), is typically accomplished while observing a slight NCO excess over the reactive hydroxy or amine compounds. At the end point of the reaction, as a result of the attainment of a target viscosity, there always are residues of active isocyanate remaining. These residues must be blocked so that there is no reaction with large polymer chains. Such a reaction leads to the three-dimensional crosslinking and gelling of the batch. A solution of that kind can no longer be processed. Typically the batches contain high quantities of alcohols. These alcohols block the remaining isocyanate groups within a number of hours of standing or stirring of the batch at room temperature.

If the residual isocyanate content has been blocked during the preparation of the polyurethaneureas that are essential to the invention, they also have, as synthesis components, monomers f) which are in each case located at the chain ends and cap them.

These synthesis components derive on the one hand from monofunctional compounds that are reactive with NCO groups, such as monoamines, especially mono-secondary amines, or monoalcohols. Examples that may be mentioned here include ethanol, n-butanol, ethylene glycol monobutyl ether, 2-ethylhexanol, 1-octanol, 1-dodecanol, 1-hexadecanol, methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine and suitable substituted derivatives thereof.

Since the building blocks f) are used in the polyurethaneureas that are essential to the invention essentially in order to destroy the NCO excess, the amount required is dependent essentially on the amount of the NCO excess, and cannot be specified in general terms.

Preferably these building blocks are omitted during the synthesis. In that case, unreacted isocyanate is preferably converted to terminal urethanes by solvent alcohols that are present at very high concentrations.

For preparing the polyurethane solutions of the invention, the polycarbonate polyol component a), the polyisocyanate, the monofunctional polyether alcohol and, where appropriate, the polyol, are reacted with one another in the melt or in solution until all of the hydroxyl groups have been consumed.

The stoichiometry used in this case between the individual synthesis components participating in the reaction is a product of the proportions mentioned above.

The reaction takes place at a temperature of preferably 60 to 110° C., more preferably 75 to 110° C., in particular 90 to 110° C., with preference being given to temperatures around 110° C. on account of the rate of the reaction. Higher temperatures can likewise be employed, but then, in certain cases, and dependant on the individual constituents used, there is a risk of decomposition events and instances of discoloration occurring in the resultant polymer.

In the case of the prepolymer of isocyanate and all of the components having hydroxyl groups, reaction in the melt is preferred, albeit with a risk of excessive viscosities on the part of the fully reacted mixtures. In such cases it is also advisable to add solvents. However, there ought as far as possible to be not more than approximately 50% by weight of solvents present, since otherwise the dilution significantly retards the reaction rate.

In the case of the reaction of isocyanate and the components having hydroxyl groups, the reaction can take place in the melt in a period of 1 hour to 24 hours. Small additions of solvent lead to a retardation, but the reaction times are within the same time periods.

The sequence of the addition and/or reaction of the individual constituents may deviate from the sequence indicated above. This may be of advantage in particular when the mechanical properties of the resultant coatings are to be modified. Where, for example, all of the components having hydroxyl groups are reacted simultaneously, a mixture of hard segments and soft segments is produced. Where, for example, the low molecular weight polyol is added after the polycarbonate polyol component, defined blocks are obtained, which may result in different properties in the resulting coatings. The present invention is therefore not confined to an arbitrary sequence of the addition and/or reaction of the individual constituents of the polyurethane coating.

The further solvent is added and the chain extender diamine and/or the dissolved chain extender amino alcohol (synthesis component (d)), in solution where appropriate, is or are added.

The further addition of the solvent takes place preferably in steps, in order not to retard the reaction unnecessarily, as would happen if the entire amount of solvent were to be added, for example, at the start of the reaction. Furthermore, a high solvent content at the beginning of the reaction dictates a relatively low temperature, which is at least co-determined by the nature of the solvent. This leads as well to the retardation of the reaction.

When the target viscosity has been obtained, the remaining residues of NCO can be blocked by a monofunctional aliphatic amine. The isocyanate groups that remain are preferably blocked by reaction with the alcohols that are present in the solvent mixture.

Suitable solvents for the preparation and application of the polyurethaneurea solutions of the invention include all conceivable solvents and solvent mixtures such as dimethylformamide, N-methylacetamide, tetramethylurea, N-methylpyrrolidone, aromatic solvents such as toluene, linear and cyclic esters, ethers, ketones and alcohols. Examples of esters and ketones are, for example, ethyl acetate, butyl acetate, acetone, γ-butyrolactone, methyl ethyl ketone and methyl isobutyl ketone.

Preference is given to mixtures of alcohols with toluene. Examples of the alcohols which are used together with the toluene are ethanol, n-propanol, isopropanol and 1-methoxy-2-propanol.

In general the amount of solvent used in the reaction is such as to give approximately 10% to 50% strength by weight solutions, more preferably approximately 15% to 45% strength by weight solutions, with particular preference approximately 20% to 40% strength solutions.

The solids content of the polyurethane solutions is generally in the range from 5 to 60% by weight, preferably 10 to 40% by weight. For coating experiments, the polyurethane solutions can be diluted arbitrarily with toluene/alcohol mixtures in order to allow variable adjustment of the thickness of the coating. All concentrations from 1% to 60% by weight are possible; concentrations in the 1% to 40% by weight range are preferred.

In this context it is possible to achieve any desired coat thicknesses, such as for example from a few hundred nm up to a few 100 μm, with higher and lower thicknesses also being possible in the context of the present invention.

The polyurethaneurea solutions of the invention may further comprise additives and constituents that are customary for the particular end use.

One example of such are pharmacological actives, medicaments and additives, which promote the release of pharmacological actives ("drug-eluting additives").

Pharmacological actives and medicaments which can be used in the coatings of the invention on the medical devices and which therefore may be present in the solutions according to the invention are, for example, thromboresistant agents, antibiotic agents, anti-tumour agents, growth hormones, antiviral agents, antiangiogenic agents, angiogenic agents, antimitotic agents, anti-inflammatory agents, cell cycle regulators, genetic agents, hormones and also their homologues, derivatives, fragments, pharmaceutical salts and combinations thereof.

Specific examples of such pharmacological actives and medicaments hence include thromboresistant (non-thrombogenic) agents and other agents for suppressing an acute thrombosis, stenosis or late re-stenosis of the arteries, examples being heparin, streptokinase, urokinase, tissue plasminogen activator, anti-thromboxan-$B_2$ agent; anti-B-thromoboglobulin, prostaglandin-E, aspirin, dipyridimol, anti-thromboxan-$A_2$ agent, murine monoclonal antibody 7E3, triazolopyrimidine, ciprostene, hirudin, ticlopidine, nicorandil, etc. A growth factor likewise may be utilized as a medicament in order to suppress subintimal fibromuscular hyperplasia of the arterial stenosis site, or any other cell growth inhibitor can be utilized at the stenosis site.

The pharmacological active or medicament may also be composed of a vasodilator, in order to counteract vasospasm—for example, an antispasm agent such as papaverine. The medicament may be a vasoactive agent per se, such as calcium antagonists, or α- and β-adrenergic agonists or antagonists. In addition the therapeutic agent may be a biological adhesive such as cyanoacrylate in medical grade or fibrin, which is used, for example, for bonding a tissue valve to the wall of a coronary artery.

The therapeutic agent may further be an antineoplastic agent such as 5-fluorouracil, preferably with a controlling releasing vehicle for the agent, (for example, for the use of an ongoing controlled releasing antineoplastic agent at a tumour site).

The therapeutic agent may be an antibiotic, preferably in combination with a controlling releasing vehicle for ongoing release from the coating of a medical device at a localized focus of infection within the body. Similarly, the therapeutic agent may comprise steroids for the purpose of suppressing inflammation in localized tissue, or for other reasons.

Specific examples of suitable medicaments include the following:

(a) heparin, heparin sulphate, hirudin, hyaluronic acid, chondroitin sulphate, dermatan sulphate, keratin sulphate, lytic agents, including urokinase and streptokinase, their homologues, analogues, fragments, derivatives and pharmaceutical salts thereof;

(b) antibiotic agents such as penicillins, cephalosporins, vacomycins, aminoglycosides, quinolones, polymyxins, erythromycins; tetracyclines, chloramphenicols, clindamycins, lincomycins, sulphonamides, their homologues, analogues, derivatives, pharmaceutical salts and mixtures thereof;

(c) paclitaxel, docetaxel, immunosuppressants such as sirolimus or everolimus, alkylating agents, including mechlorethamine, chlorambucil, cyclophosphamide, melphalane and ifosfamide; antimetabolites, including methotrexate, 6-mercaptopurine, 5-fluorouracil and cytarabine; plant alkoids, including vinblastin; vincristin and etoposide; antibiotics, including doxorubicin, daunomycin, bleomycin and mitomycin; nitrosurea, including carmustine and lomustine; inorganic ions, including cisplatin; biological reaction modifiers, including interferon; angiostatins and endostatins; enzymes, including asparaginase; and hormones, including tamoxifen and flutamide, their homologues, analogues, fragments, derivatives, pharmaceutical salts and mixtures thereof;

(d) antiviral agents such as amantadine, rimantadine, rabavirin, idoxuridine, vidarabin, trifluridine, acyclovir, ganciclorir, zidovudine, phosphonoformates, interferons, their homologues, analogues, fragments, derivatives, pharmaceutical salts and mixtures thereof; and e) antiflammatory agents such as, for example, ibuprofen, dexamethasone or methylprednisolone.

To generate surfaces having infestation-inhibiting properties, the coating compositions of the invention may comprise the active infestation inhibitors known from the prior art. Their presence generally boosts the already outstanding infestation-inhibiting properties of the surfaces produced with the coating compositions of the invention themselves.

Further additions such as, for example, antioxidants or pigments may likewise be used. Additionally it is possible, where appropriate, to use further additions as well, such as hand agents, dyes, matting agents, UV stabilizers, light stabilizers, hydrophobicizers and/or flow control assistants.

The polyurethaneurea solutions of the invention can be used to form a coating for example on a medical device.

The teen "medical device" is to be understood broadly in the context of the present invention. Suitable, non-limiting examples of medical devices (including instruments) are contact lenses; cannulas; catheters, for example urological catheters such as urinary catheters or ureteral catheters; central venous catheters; venous catheters or inlet or outlet catheters; dilation balloons; catheters for angioplasty and biopsy; catheters used for introducing a stent, an embolism filter or a vena caval filter; balloon catheters or other expandable medical devices; endoscopes; laryngoscopes; tracheal devices such as endotracheal tubes, respirators and other tracheal aspiration devices; bronchoalveolar lavage catheters; catheters used in coronary angioplasty; guide rods, insertion guides and the like; vascular plugs; pacemaker components; cochlear implants; dental implant tubes for feeding, drainage tubes; and guide wires;

The solutions according to the invention may be used, furthermore, for producing protective coatings, for example for gloves, stents and other implants; external (extracorporeal) blood lines (blood-carrying tubes); membranes; for example for dialysis; blood filters; devices for circulatory support; dressing material for wound management; urine bags and stoma bags. Also included are implants which comprise a medically active agent, such as medically active agents for stents or for balloon surfaces or for contraceptives.

Typically the medical device is formed from catheters, endoscopes, laryngoscopes, endotracheal tubes, feeding tubes, guide rods, stents, and other implants.

In addition to the hydrophilic properties of improving the lubricity, the coating compositions provided in accordance with the invention are also notable for a high level of blood compatibility. This makes working with these coatings advantageous in blood contact in particular. The materials exhibit reduced coagulation tendency in blood contact as compared with polymers of the prior art.

Systems which release active substances and are based on the hydrophilic coating materials of the invention are also conceivable outside medical technology, as for example for applications in crop protection as a carrier material for actives. The entire coating may in that case be considered an active-releasing system and may be used, for example, to coat seed (seed grains). As a result of the hydrophilic properties of the coating, the active it contains is able to emerge in the moist earth and develop its intended effect, without adversely affecting the capacity of the seed to germinate. In the dry state, however, the coating composition binds the active securely to the seed, and so, for example, the active is not detached, when the seed grain is being fired into the soil by the broadcasting machine; as a result of such detachment, the active could develop unwanted effects, for example, on the fauna that are present (jeopardizing bees by insecticides intended per se to prevent the attack of insects on the seed grain in the soil).

Beyond their application as a coating for medical devices, the polyurethane solutions according to the invention can also be utilized for further technical applications in the non-medical sector.

Thus, the polyurethane solutions according to the invention serve for producing coatings as protection of surfaces against fogging with moisture, for the production of easy-to-clean or self-cleaning surfaces. These hydrophilic coatings also reduce the pick-up of dirt and prevent the formation of water spots. Conceivable applications in the exterior sector are, for example, windows and roof lights, glass facades or Plexiglas roofs. In the interior sector, materials of this kind can be utilized for the coating of surfaces of sanitary equipment. Further applications are the coating of spectacle lenses or of packaging materials such as food packaging for the purpose of preventing moisture fogging or droplet formation due to condensed water.

The polyurethane solutions according to the invention are also suitable for treating surfaces in contact with water for the purpose of reducing infestation. This effect is also referred to as the antifouling effect. One very important application of this antifouling effect is in the area of the underwater coatings on ships' hulls. Ships' hulls without an antifouling treatment very quickly become infested by marine organisms, leading to increased friction and hence to a reduction in the possible speed and a higher consumption of fuel. The coating materials of the invention reduce or prevent infestation by marine organisms, and prevent the above-described disadvantages of this infestation. Further applications in the area of antifouling coatings are articles for fishing such as fishing-nets and also all metallic substrates in underwater use, such as pipelines, offshore drilling platforms, locks and lock gates, etc. Hulls which have surfaces generated with the coating materials of the invention, especially below the water line, also possess a reduced frictional resistance, and so ships thus equipped either have a reduced fuel consumption or achieve higher speeds. This is of interest in particular in the sporting boat sector and in yacht building.

A further important field for application of the abovementioned hydrophilic coating materials is the printing industry. By means of the coatings of the invention, hydrophobic surfaces can be made hydrophilic and as a result can be printed with polar printing inks, or can be printed using ink-jet technology.

A further field for application of the hydrophilic coatings of the invention is in formulations for cosmetic applications.

Coatings of the polyurethane solutions according to the invention can be applied by means of a variety of methods. Examples of suitable coating techniques for these solutions include knife coating, printing, transfer coating, spraying, spin coating or dipping.

A wide variety of substrates can be coated, such as metals, textiles, ceramics and plastics. Preference is given to coating medical devices manufactured from plastic or metal. Examples of metals that can be mentioned include the following: medical stainless steel and nickel titanium alloys. Many polymer materials are conceivable from which the medical devices may be constructed, examples being polyamide; polystyrene; polycarbonate; polyethers; polyesters; polyvinyl acetate; natural and synthetic rubbers; block copolymers of styrene and unsaturated compounds such as ethylene, butylene and isoprene; polyethylene or copolymers of polyethylene and polypropylene; silicone; polyvinyl chloride (PVC) and polyurethanes. For better adhesion of the hydrophilic polyurethanes to the medical device, further suitable coatings may be applied as a base before these hydrophilic coating materials are applied.

EXAMPLES

The NCO content of the resins described in the inventive and comparative examples was determined by titration in accordance with DIN EN ISO 11909.

The solids contents were determined in accordance with DIN-EN ISO 3251. Polyurethane dispersion (1 g) was dried at 115° C. at a constant weight (15-20 min) using an infrared drier.

The average particle sizes of the polyurethane dispersions were measured using the High Performance Particle Sizer (HPPS 3.3) from Malvern Instruments.

Unless noted otherwise, the amounts reported in % are to be understood as % by weight and relate to the aqueous dispersion obtained.

The tensile strengths were determined in accordance with DIN 53504.

Viscosity measurements were carried out using the Physics MCR 51 Rheometer from Anton Paar GmbH, Ostfildern, Germany.

| Substances used and abbreviations: | |
| --- | --- |
| Desmophen C2200: | polycarbonate polyol, OH number 56 mg KOH/g, number-average molecular weight 2000 g/mol (Bayer MaterialScience AG, Leverkusen, DE) |
| Desmophen C1200: | polycarbonate polyol, OH number 56 mg KOH/g, number-average molecular weight 2000 g/mol (Bayer MaterialScience AG, Leverkusen, DE) |
| Desmophen XP 2613 | polycarbonate polyol, OH number 56 mg KOH/g, number-average molecular weight 2000 g/mol (Bayer MaterialScience AG, Leverkusen, DE) |
| Polyether LB 25: | monofunctional polyether based on ethylene oxide/propylene oxide, number-average molecular weight 2250 g/mol, OH number 25 mg KOH/g (Bayer MaterialScience AG, Leverkusen, DE) |
| TCD Alcohol DM | 3(4),8(9)-bis(hydroxymethyl)tricyclo(5.2.1.0/2.6) decane/tricyclodecanedimethanol from Celanese Corp., Dallas, USA |

Example 1

Preparation of a cycloaliphatic polycarbonate diol based on TCD alcohol DM with a number-average molecular weight of 1300 g/mol A 16 l pressure reactor with top-mounted distillation attachment, stirrer and receiver was charged with 5436 g of TCD Alcohol DM along with 1.2 g of yttrium(III) acetylacetonate and also 3810 g of dimethyl carbonate at 80° C. Subsequently, under a nitrogen atmosphere, the reaction mixture was heated to 135° C. over 2 h and maintained there with stirring for 24 h, during which the pressure climbed to 6.3 bar (absolute). It was then cooled to 60° C. and air was admitted. The methanol elimination product was then removed by distillation in a mixture with dimethyl carbonate, the temperature being raised in steps to 150° C. The mixture was then stirred at 150° C. for a further 4 hours, subsequently heated to 180° C., and then stirred at 180° C. for a further 4 h. The temperature was then reduced to 90° C. and a stream of nitrogen (5 l/h) was passed through the reaction mixture, during which the pressure was lowered to 20 mbar. Thereafter the temperature was increased to 180° C. over 4 h and held there for 6 h. In the course of this operation, methanol was removed further from the reaction mixture, in a mixture with dimethyl carbonate.

After air had been admitted and the reaction mixture cooled to room temperature, a yellowish solid polycarbonate diol was obtained that had the following characteristics:

$M_n$=1290 g/mol; OH number=87 mg KOH/g

Example 2

Preparation of a cycloaliphatic polycarbonate diol based on TCD Alcohol DM with a number-average molecular weight of 1000 g/mol Procedure as in Example 1, using 5436 g of TCD Alcohol DM, 1.2 g of yttrium(III) acetylacetonate and 2931 g of dimethyl carbonate.

This gave a yellowish polycarbonate diol of high viscosity that had the following characteristics: $M_n$=1000 g/mol; OH number=112 mg KOH/g

Example 3

Preparation of a cycloaliphatic polycarbonate diol based on TCD Alcohol DM with a number-average molecular weight of about 500 g/mol Procedure as in Example 1, using 7790 g of TCD Alcohol DM, 1.68 g of yttrium(III) acetylacetonate and 3096 g of dimethyl carbonate.

This gave a yellowish polycarbonate diol of high viscosity that had the following characteristics: $M_n$=496 g/mol; OH number=226 mg KOH/g; viscosity at 75° C.=138 400 mPas.

Example 4

Preparation of a (cyclo)aliphatic polycarbonate diol based on TCD Alcohol DM and 1,4-butanediol with a number-average molecular weight of about 1000 g/mol Procedure as in Example 1, using 5951 g of TCD Alcohol DM, 2732 g of 1,4-butanediol, 2.0 g of yttrium(III) acetylacetonate and 6842 g of dimethyl carbonate.

This gave a colourless polycarbonate diol that had the following characteristics: $M_n$=943 g/mol; OH number=119 mg KOH/g; viscosity at 75° C.=15 130 mPas.

Example 5: (Comparative)

195.4 g of Desmophen C 2200, 30.0 g of LB 25 and 47.8 g of 4,4'-bis(isocyanato-cyclohexyl)methane ($H_{12}$MDI) were reacted at 110° C. to a constant NCO content of 2.4%. The mixture was allowed to cool and was diluted with 350.0 g of toluene and 200 g of isopropanol. At room temperature, a solution of 11.8 g of isophoronediamine in 94.0 g of 1-methoxypropan-2-ol was added. After the end of the increase in molar weight, and the attainment of the desired viscosity range, stirring was continued for 5 hours in order to block the residual isocyanate content with isopropanol. This gave 929 g of a 31.9% strength solution of polyurethaneurea in toluene/isopropanol/1-methoxypropan-2-ol with a viscosity of 37 100 mPas at 22° C.

Example 6: (Inventive)

175.8 g of Desmophen C 2200, 12.7 g of polycarbonate diol of Example 1, 30.0 g of LB 25 and 47.8 g of 4,4'-bis(isocyanatocyclohexyl)methane ($H_{12}$MDI) were reacted at 110° C. to a constant NCO content of 2.5%. The mixture was allowed to cool and was diluted with 340.0 g of toluene and 200 g of isopropanol. At room temperature, a solution of 12.4 g of isophoronediamine in 93.0 g of 1-methoxypropan-2-ol was added. After the end of the increase in molar weight, and the attainment of the desired viscosity range, stirring was continued for 4 hours in order to block the residual isocyanate content with isopropanol. This gave 912 g of a 30.8% strength solution of polyurethaneurea in toluene/isopropanol/1-methoxypropan-2-ol with a viscosity of 28 500 mPas at 22° C.

Example 7: (Inventive)

146.6 g of Desmophen C 2200, 31.7 g of polycarbonate diol of Example 1, 30.0 g of LB 25 and 47.8 g of 4,4'-bis(isocyanatocyclohexyl)methane ($H_{12}$MDI) were reacted at 110° C. to a constant NCO content of 2.5%. The mixture was allowed to cool and was diluted with 330.0 g of toluene and 200 g of isopropanol. At room temperature, a solution of 12.5 g of isophoronediamine in 98.0 g of 1-methoxypropan-2-ol was added. After the end of the increase in molar weight, and the attainment of the desired viscosity range, stirring was continued for 4 hours in order to block the residual isocyanate content with isopropanol. This gave 897 g of a 30.4% strength solution of polyurethaneurea in toluene/isopropanol/1-methoxypropan-2-ol with a viscosity of 20 600 mPas at 22° C.

Example 8: (Inventive)

97.8 g of Desmophen C 2200, 63.6 g of polycarbonate diol of Example 1, 30.0 g of LB 25 and 47.8 g of 4,4'-bis(isocyanatocyclohexyl)methane ($H_{12}$MDI) were reacted at 110° C. to a constant NCO content of 2.7%. The mixture was allowed to cool and was diluted with 335.0 g of toluene and 185 g of isopropanol. At room temperature, a solution of 12.7 g of isophoronediamine in 99.0 g of 1-methoxypropan-2-ol was added. After the end of the increase in molar weight, and the attainment of the desired viscosity range, stirring was continued for 2 hours in order to block the residual isocyanate content with isopropanol. This gave 871 g of a 29.3% strength solution of polyurethaneurea in toluene/isopropanol/1-methoxypropan-2-ol with a viscosity of 17 000 mPas at 22° C.

Example 9: (Inventive)

175.8 g of Desmophen C 2200, 9.8 g of polycarbonate diol of Example 4, 30.0 g of LB 25 and 47.8 g of 4,4'-bis(isocyanatocyclohexyl)methane ($H_{12}$MDI) were reacted at 110° C. to a constant NCO content of 2.5%. The mixture was allowed to cool and was diluted with 350.0 g of toluene and 200 g of isopropanol. At room temperature, a solution of 12.3 g of isophoronediamine in 98.0 g of 1-methoxypropan-2-ol was added. After the end of the increase in molar weight, and the attainment of the desired viscosity range, stirring was continued for 5 hours in order to block the residual isocyanate content with isopropanol. This gave 924 g of a 30.1% strength solution of polyurethaneurea in toluene/isopropanol/1-methoxypropan-2-ol with a viscosity of 18 900 mPas at 22° C.

Example 10: (Inventive)

146.6 g of Desmophen C 2200, 24.4 g of polycarbonate diol of Example 4, 30.0 g of LB 25 and 47.8 g of 4,4'-bis(isocyanatocyclohexyl)methane ($H_{12}$MDI) were reacted at 110° C. to a constant NCO content of 2.6%. The mixture was allowed to cool and was diluted with 335.0 g of toluene and 190 g of isopropanol. At room temperature, a solution of 12.5 g of isophoronediamine in 100.0 g of 1-methoxypropan-2-ol was added. After the end of the increase in molar weight, and the attainment of the desired viscosity range, stirring was continued for 4 hours in order to block the residual isocyanate content with isopropanol. This gave 886 g of a 30.1% strength solution of polyurethaneurea in toluene/isopropanol/1-methoxypropan-2-ol with a viscosity of 20 600 mPas at 22° C.

Example 11: (Inventive)

97.8 g of Desmophen C 2200, 48.9 g of polycarbonate diol of Example 4, 30.0 g of LB 25 and 47.8 g of 4,4'-bis(isocyanatocyclohexyl)methane ($H_{12}$MDI) were reacted at 110° C. to a constant NCO content of 2.8%. The mixture was allowed to cool and was diluted with 325.0 g of toluene and 175 g of isopropanol. At room temperature, a solution of 12.7 g of isophoronediamine in 98.0 g of 1-methoxypropan-2-ol was added. After the end of the increase in molar weight, and the attainment of the desired viscosity range, stirring was continued for 4 hours in order to block the residual isocyanate content with isopropanol. This gave 835 g of a 29.0% strength solution of polyurethaneurea in toluene/isopropanol/1-methoxypropan-2-ol with a viscosity of 27 400 mPas at 22° C.

Example 12

Contact Angles and 100% Moduli of Comparative Example 4 Against Inventive Examples 5-10

1. Production of the Coatings for the Measurement of the Static Contact Angle

The coatings for the measurement of the static contact angle were produced on glass slides measuring 25×75 mm using a spin coater (RC5 Gyrset 5, Karl Süss, Garching, Germany). For this purpose, a slide was clamped on to the sample plate of the spin coater and covered homogeneously with about 2.5-3 g of organic 15% strength polyurethane solution. All of the organic polyurethane solutions were diluted to a polymer content of 15% using a solvent mixture of 65% by weight toluene and 35% by weight isopropanol. Rotation of the sample plate at 1300 revolutions per minute for 20 seconds gave a homogeneous coating, which was dried at 100° C. for 1 h and then at 50° C. for 24 h. The coated slides obtained were subjected directly to a contact angle measurement.

A static contact angle measurement was performed on the resulting coatings on the slides. Using the video contact angle measuring instrument OCA20 from Dataphysics, with computer-controlled injection, 10 drops of Millipore water were applied to the specimen, and their static wetting contact angle was measured. Beforehand, using an antistatic drier, the static charge (if present) on the sample surface was removed.

2. Production of the Coatings for the Measurement of the 100% Modulus

Films are produced on release paper using a 200 μm doctor blade, and are dried at 100° C. for 15 minutes. This is followed by drying at 100° C. for 15 minutes. Punched shapes are investigated in accordance with DIN 53504.

3. Results of Investigation

TABLE 1

Contact angles and 100% moduli of the films from materials of Examples 5-11

| Example No. | Contact angle (°) | 100% modulus (N/mm$^2$) |
| --- | --- | --- |
| Comparative Example 5 | 21 | 2.3 |
| Example 6 | 33 | 2.5 |
| Example 7 | 33 | 2.6 |
| Example 8 | 24 | 6.4 |
| Example 9 | 30 | 2.5 |
| Example 10 | 30 | 2.9 |
| Example 11 | 41 | 4.3 |

Inventive Examples 6 to 11 differ in that, in comparison to comparative Example 5, some of the polycarbonate diol Desmophen C2200 was replaced by the polycarbonate diol essential to the invention. In the form of a coating, the materials have hydrophilic properties similar to those of comparative Example 5. The 100% moduli are all higher than that of comparative Example 5.

Example 13: (Comparative)

195.4 g of Desmophen C 2200, 30.0 g of LB 25 and 47.8 g of 4,4'-bis(isocyanato-cyclohexyl)methane ($H_{12}MDI$) were reacted at 110° C. to a constant NCO content of 2.4%. The mixture was allowed to cool and was diluted with 350.0 g of toluene and 200 g of isopropanol. At room temperature, a solution of 13.3 g of isophoronediamine in 100 g of 1-methoxypropan-2-ol was added. After the end of the increase in molar weight, and the attainment of the desired viscosity range, stirring was continued for 4.5 hours in order to block the residual isocyanate content with isopropanol. This gave 936 g of a 30.6% strength solution of polyurethaneurea in toluene/isopropanol/1-methoxypropan-2-ol with a viscosity of 10 200 mPas at 22° C.

Example 14: (Inventive)

97.8 g of Desmophen C 1200, 24.5 g of polycarbonate diol of Example 3, 30.0 g of LB 25 and 47.8 g of 4,4'-bis(isocyanatocyclohexyl)methane ($H_{12}MDI$) were reacted at 110° C. to a constant NCO content of 3.3%. The mixture was allowed to cool and was diluted with 250.0 g of toluene and 150 g of isopropanol. At room temperature, a solution of 13.1 g of isophoronediamine in 100 g of 1-methoxypropan-2-ol was added. After the end of the increase in molar weight, and the attainment of the desired viscosity range, stirring was continued for 3 hours in order to block the residual isocyanate content with isopropanol. This gave 713 g of a 30.4% strength solution of polyurethaneurea in toluene/isopropanol/1-methoxypropan-2-ol with a viscosity of 29 200 mPas at 22° C.

Example 15: (Inventive)

130.2 g of Desmophen C 1200, 16.3 g of polycarbonate diol of Example 3, 30.0 g of LB 25 and 47.8 g of 4,4'-bis(isocyanatocyclohexyl)methane ($H_{12}MDI$) were reacted at 110° C. to a constant NCO content of 2.9%. The mixture was allowed to cool and was diluted with 320.0 g of toluene and 170 g of isopropanol. At room temperature, a solution of 13.2 g of isophoronediamine in 99 g of 1-methoxypropan-2-ol was added. After the end of the increase in molar weight; and the attainment of the desired viscosity range, stirring was continued for 3 hours in order to block the residual isocyanate content with isopropanol. This gave 827 g of a 29.0% strength solution of polyurethaneurea in toluene/isopropanol/1-methoxypropan-2-ol with a viscosity of 31 900 mPas at 22° C.

Example 16

Contact Angles and 100% Moduli of Comparative Example 13 Versus Inventive Examples 14 and 15

The production of the coatings and also the determination of the contact angles and 100% moduli take place as described in Example 12.

TABLE 2

Contact angles and 100% moduli of the films of materials of Examples 13, 14 and 15

| Example No. | Contact angle (°) | 100% modulus (N/mm$^2$) |
|---|---|---|
| Comparative Example 13 | 11 | 1.8 |
| Example 14 | 18 | 6.1 |
| Example 15 | 18 | 5.0 |

In comparison to comparative Example 17, inventive Examples 18, 19 and 20 include fractions of the polycarbonate diol essential to the invention. The surface of the coating continues to be very hydrophilic, while the 100% modulus goes up by approximately three times.

Example 17: (Comparative)

195.4 g of Desmophen C 2200, 40.0 g of LB 25 and 47.8 g of 4,4'-bis(isocyanato-cyclohexyl)methane ($H_{12}MDI$) were reacted at 110° C. to a constant NCO content of 2.2%. The mixture was allowed to cool and was diluted with 350.0 g of toluene and 200 g of isopropanol. At room temperature, a solution of 12.0 g of isophoronediamine in 100.0 g of 1-methoxypropan-2-ol was added. After the end of the increase in molar weight, and the attainment of the desired viscosity range, stirring was continued for 4 hours in order to block the residual isocyanate content with isopropanol. This gave 945 g of a 31.6% strength solution of polyurethaneurea in toluene/isopropanol/1-methoxypropan-2-ol with a viscosity of 19 300 mPas at 22° C.

Example 18: (Inventive)

97.8 g of Desmophen C 2200, 48.9 g of polycarbonate diol of Example 4, 40.0 g of LB 25 and 47.8 g of 4,4'-bis(isocyanatocyclohexyl)methane ($H_{12}MDI$) were reacted at 110° C. to a constant NCO content of 2.7%. The mixture was allowed to cool and was diluted with 320.0 g of toluene and 180 g of isopropanol. At room temperature, a solution of 12.3 g of isophoronediamine in 100 g of 1-methoxypropan-2-ol was added. After the end of the increase in molar weight, and the attainment of the desired viscosity range, stirring was continued for 4 hours in order to block the residual isocyanate content with isopropanol. This gave 847 g of a 29.6% strength solution of polyurethaneurea in toluene/isopropanol/1-methoxypropan-2-ol with a viscosity of 9600 mPas at 22° C.

Example 19: (Inventive)

97.8 g of Desmophen C 2200, 24.5 g of polycarbonate diol of Example 3, 40.0 g of LB 25 and 47.8 g of 4,4'-bis(isocyanatocyclohexyl)methane ($H_{12}MDI$) were reacted at 110° C. to a constant NCO content of 3.0%. The mixture was allowed to cool and was diluted with 300.0 g of toluene and 180 g of isopropanol. At room temperature, a solution of 12.5 g of isophoronediamine in 100 g of 1-methoxypropan-2-ol was added. After the end of the increase in molar weight, and the attainment of the desired viscosity range, stirring was continued for 4.5 hours in order to block the residual isocyanate content with isopropanol. This gave 803 g of a 28.4% strength solution of polyurethaneurea in toluene/isopropanol/1-methoxypropan-2-ol with a viscosity of 3250 mPas at 22° C.

Example 20: (Inventive)

97.8 g of Desmophen C 2200, 48.9 g of polycarbonate diol of Example 2, 40.0 g of LB 25 and 47.8 g of 4,4'-bis(isocyanatocyclohexyl)methane ($H_{12}MDI$) were reacted at 110° C. to a constant NCO content of 2.7%. The mixture was allowed to cool and was diluted with 320.0 g of toluene and 200 g of isopropanol. At room temperature, a solution of 12.3 g of isophoronediamine in 100 g of 1-methoxypropan-2-ol was added. After the end of the increase in molar weight, and the attainment of the desired viscosity range, stirring was continued for 3.5 hours in order to block the residual isocyanate content with isopropanol. This gave 867 g of a 28.9% strength solution of polyurethaneurea in toluene/isopropanol/1-methoxypropan-2-ol with a viscosity of 6200 mPas at 22° C.

Example 21

Contact Angles and 100% Moduli of Comparative Example 17 Versus Inventive Examples 18, 19 and 20

The production of the coatings and also the determination of the contact angles and 100% moduli take place as described in Example 12.

TABLE 2

Contact angles and 100% moduli of the films of materials of Examples 17, 18, 19 and 20

| Example No. | Contact angle (°) | 100% modulus (N/mm²) |
|---|---|---|
| Comparative Example 17 | 14 | 2.7 |
| Example 18 | 20 | 4.6 |
| Example 19 | 21 | 6.0 |
| Example 20 | 18 | 6.3 |

In comparison to comparative Example 17, inventive Examples 18, 19 and 20 include fractions of a polycarbonate diol essential to the invention. The surface of the coating continues to be very hydrophilic, while the 100% modulus goes up by approximately three times.

The invention claimed is:
1. A polyurethaneurea solution comprising a polyurethaneurea having a structural unit of the formula (I)

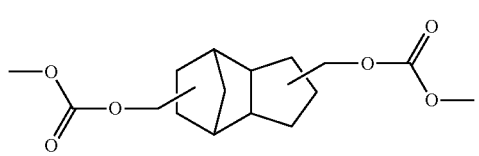

and terminated with at least one copolymer unit selected from the group consisting of a polyethylene oxide, a polypropylene oxide, and mixtures thereof, and wherein the polyurethaneurea solution is obtained by reacting
 a. a polycarbonate polyol a1) which is obtained by reacting a carbonic acid derivative with a difunctional alcohol of the formula (II)

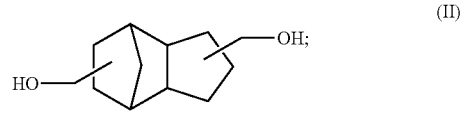

and
 a polycarbonate polyol a2) having an average hydroxyl functionality from 1.7 to 2.3 and a molecular weight, as determined by the OH number, from 400 to 6,000 g/mol, based on hexane-1,6-diol, butane-1,4-diol or mixtures thereof,
 b. a polyisocyanate component,
 c. a polyoxyalkylene ether component,
 d. a diamine and/or amino alcohol component and,
 e. a second polyol component, wherein the second polyol component is selected from the group consisting of ethylene glycol, diethylene glycol, triethylene glycol, 1,2-propanediol, 1,3 propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenyl)propane), hydrogenated bisphenol A (2,2-bis(4-hydroxycyclohexyl)propane), trimethylolpropane, glycerol, pentaerythritol, α-hydroxybutyl-ε-hydroxycaproic esters, ω-hydroxyhexyl-γ-hydroxybutyric esters, adipic acid (β-hydroxyethyl) esters, terephthalic acid bis(β-hydroxyethyl) ester, and mixtures thereof.

2. The polyurethaneurea solution according to claim 1, wherein the polyurethaneurea is free from ionic or ionogenic groups.

3. The polyurethaneurea solution according to claim 1, wherein the copolymer unit of polyethylene oxide and polypropylene oxide that is used for termination is based on a monohydroxy-functional mixed polyalkylene oxide polyether comprising at least 40 mol % ethylene oxide units and not more than 60 mol % propylene oxide units based on the total fraction of alkylene oxide units having a number-average molecular weight from 500 g/mol to 5,000 g/mol.

4. The polyurethaneurea solution according to claim 1, wherein the polyurethaneurea has a number-average molecular weight from 5,000 to 100,000 g/mol as measured in dimethylacetamide at 30° C.

5. The polyurethaneurea solution according to claim 1, wherein the polyurethaneurea solution further comprises a solvent selected from the group consisting of dimethylformamide, N-methylacetamide, tetramethylurea, N-methylpyrrolidone, toluene, linear and cyclic esters, ethers, ketones, alcohols, and mixtures thereof.

6. The polyurethaneurea solution according to claim 5, wherein the solvent is selected from the group consisting of mixtures of toluene and ethanol, n-propanol, isopropanol, 1-methoxy-2-propanol, and mixtures thereof.

7. The polyurethaneurea solution according to claim 1, wherein the polyurethaneurea solution further comprises a pharmacological active compound.

8. A polyurethaneurea obtained from the polyurethaneurea solution according to claim 1.

9. A coating obtained from the polyurethaneurea according to claim 8.

10. A substrate coated with the coating according to claim 9.

11. The polyurethaneurea solution according to claim 1, wherein the polyurethaneurea has a number-average molecular weight from 5,000 to 100,000 g/mol as measured in dimethylacetamide at 30° C., and wherein the copolymer unit of polyethylene oxide and polypropylene oxide that is used for termination is based on a monohydroxy-functional mixed polyalkylene oxide polyether comprising at least 40 mol % ethylene oxide units and not more than 60 mol % propylene oxide units based on the total fraction of alkylene oxide units having a number-average molecular weight from 500 g/mol to 5,000 g/mol.

12. The polyurethaneurea solution according to claim 11, wherein the polyurethaneurea solution further comprises
- a. a solvent selected from the group consisting of mixtures of toluene and ethanol, n-propanol, isopropanol, 1-methoxy-2-propanol, and mixtures thereof, and
- b. a pharmacological active compound.

* * * * *